(12) United States Patent
Cantin et al.

(10) Patent No.: US 8,530,467 B2
(45) Date of Patent: Sep. 10, 2013

(54) BENZOIMIDAZOLE COMPOUNDS AND USES THEREOF

(75) Inventors: Louis-David Cantin, Montreal (CA); Xuehong Luo, Montreal (CA); Miroslaw Jerzy Tomaszewski, Montreal (CA)

(73) Assignee: Neomed Institute, Montreal, Quebec (CA)

( * ) Notice: Subject to any disclaimer, the term of this patent is extended or adjusted under 35 U.S.C. 154(b) by 0 days.

(21) Appl. No.: 13/472,825

(22) Filed: May 16, 2012

(65) Prior Publication Data

US 2012/0289504 A1 Nov. 15, 2012

Related U.S. Application Data

(63) Continuation of application No. PCT/SE2010/051269, filed on Nov. 17, 2010.

(60) Provisional application No. 61/262,263, filed on Nov. 18, 2009.

(51) Int. Cl.
*A61K 31/535* (2006.01)
*C07D 413/06* (2006.01)

(52) U.S. Cl.
USPC ........................ 514/234.5; 544/139

(58) Field of Classification Search
USPC ..................... 544/139; 514/234.5
See application file for complete search history.

(56) References Cited

U.S. PATENT DOCUMENTS 7,550,495 B2    6/2009    Page et al.

FOREIGN PATENT DOCUMENTS

| WO | WO 97/22596 | 6/1997 |
|---|---|---|
| WO | WO 97/30035 | 8/1997 |
| WO | WO 97/32856 | 9/1997 |
| WO | WO 98/13354 | 4/1998 |
| WO | WO 99/02166 | 1/1999 |
| WO | WO 00/40529 | 7/2000 |
| WO | WO 00/41669 | 7/2000 |
| WO | WO 00/47212 | 8/2000 |
| WO | WO 01/92224 | 12/2001 |
| WO | WO 01/94341 | 12/2001 |
| WO | WO 02/04434 | 1/2002 |
| WO | WO 02/08213 | 1/2002 |
| WO | WO 2008/108958 | 9/2008 |
| WO | WO 2008/136756 | 11/2008 |
| WO | WO 2009/058298 | 5/2009 |

OTHER PUBLICATIONS

Chen et al., Nature, 1995, pp. 428-431, vol. 377.
Lewis, et al., Nature, 1995, pp. 432-435, vol. 377.
Garcia-Guzman, et al., Brain Res. Mol. Brain Res., 1997, pp. 59-66, vol. 47.
Cockayne, et al., Nature, 2000, pp. 1011-1015, vol. 407.
Jarvis, et al., PNAS, 2002, pp. 17179-17184, vol. 99.
Zhong, et al., Neuroscience, 2003, pp. 667-675, vol. 120.

*Primary Examiner* — Rebecca Anderson
(74) *Attorney, Agent, or Firm* — Choate, Hall & Stewart, LLP; Charles E. Lyon; Xiaodong Li

(57) ABSTRACT

This invention generally relates to substituted benzoimidazole compounds, particularly methyl 2-((2-(2,6-difluoro-4-(methylcarbamoyl)phenyl)-5-methyl-1H-benzo[d]imidazol-1-yl)methyl)morpholine-4-carboxylate and salts thereof. This invention also relates to pharmaceutical compositions and kits comprising such a compound, uses of such a compound (including, for example, treatment methods and medicament preparations), processes for making such a compound, and intermediates used in such processes.

29 Claims, No Drawings

BENZOIMIDAZOLE COMPOUNDS AND USES THEREOF

CROSS-REFERENCE TO RELATED APPLICATION PATENT APPLICATIONS

This patent is a continuation under 35 U.S.C. §120 of International Application No. PCT/SE2010/051269 (filed 17 Nov. 2010; and published as WO2011/062550 on 26 May 2011), which, in turn, claims the benefit of priority to U.S. Provisional Patent Application No. 61/262,263 (filed Nov. 18, 2009). The entire text of each of the above patent applications is incorporated by reference into this patent.

FIELD OF THE INVENTION

This invention generally relates to substituted benzoimidazole compounds, particularly methyl 2-((2-(2,6-difluoro-4-(methylcarbamoyl)phenyl)-5-methyl-1H-benzo[d]imidazol-1-yl)methyl)morpholine-4-carboxylate and salts thereof. This invention also relates to pharmaceutical compositions and kits comprising such a compound, uses of such a compound (including, for example, treatment methods and medicament preparations), processes for making such a compound, and intermediates used in such processes.

BACKGROUND

P2X purinoreceptors are a family of ion channels that are activated by extracellular adenosine triphosphate (ATP). Purinoreceptors have been implicated in a variety of biological functions, especially those related to pain sensitivity. The P2X3 receptor subunit is a member of this family. It was originally cloned from rat dorsal root ganglia. Chen et al., *Nature*, vol. 377, pp. 428-431 (1995). The nucleotide and amino acid sequences of both rat and human P2X3 are now known. Lewis, et al., *Nature*, vol. 377, pp. 432-435 (1995); and Garcia-Guzman, et al., *Brain Res. Mol. Brain. Res.*, vol. 47, pp. 59-66 (1997).

P2X3 is reportedly involved in afferent pathways controlling urinary bladder volume reflexes. Consequently, inhibiting P2X3 may have therapeutic potential for treating disorders of urine storage and voiding, such as overactive bladder. Cockayne, et al., *Nature*, vol. 407, pp. 1011-1015 (2000).

P2X3 also is selectively expressed on nociceptive, small diameter sensory neurons (i.e., neurons that are stimulated by pain or injury), which is consistent with a role in pain sensitivity. And blocking P2X3 receptors has been reported to be analgesic in animal models of chronic inflammatory and neuropathic pain. Jarvis, et al., *PNAS*, 99, 17179-17184 (2002). It is, therefore, believed that a method for reducing the P2X3 level or activity would be useful for modulating pain sensation in a subject suffering from pain.

Various other disorders also have been discussed as being treatable using compounds having P2X3 activity. See, e.g., WO2008/136756.

P2X3 also is capable of forming P2X2/3 heterodimers with P2X2, which is another member of the P2X purinergic ligand-gated ion channel family. P2X2/3 is highly expressed on the terminals (central and peripheral) of sensory neurons. Chen, et al., Nature, vol. 377, pp. 428-431 (1995). Results from recent studies also suggest that P2X2/3 is predominantly expressed (over P2X3) in bladder sensory neurons, and are likely to play a role in sensing of urinary bladder filling and nociception. Zhong, et al., Neuroscience, vol. 120, pp. 667-675 (2003).

In view of the foregoing, there is a need for new P2X3 and/or P2X2/3 receptor ligands, particularly antagonists, that may be useful and safe for treating various disorders related to P2X3 and/or P2X2/3.

SUMMARY OF THE INVENTION

This invention comprises, inter alia, benzoimidazole compounds; treatment methods using the benzoimidazole compounds (e.g., use of the benzoimidazole to treat various disorders and as pharmacological tools); use of the benzoimidazole compounds to make medicaments; compositions comprising the benzoimidazole compounds (e.g., pharmaceutical compositions); methods for manufacturing the benzoimidazole compounds; and intermediates used in such manufacturing methods.

Briefly, this invention is directed, in part, to the compound of Formula I or a salt thereof. Formula I corresponds to:

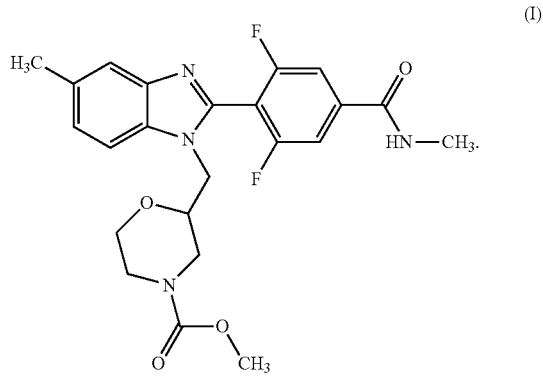 [SMILES: CNC(=O)c1cc(F)c(-c2nc3cc(C)ccc3n2CC2CN(C(=O)OC)CCO2)c(F)c1]

This invention also is directed, in part, to a pharmaceutical composition that comprises the compound of Formula I or a pharmaceutically acceptable salt thereof. In general, such a composition additionally comprises a pharmaceutically acceptable inert ingredient (inert ingredients are sometimes collectively identified in this patent as "carriers, diluents, or excipients"). The composition may further comprise one or more other ingredients. For example, the composition may further comprise one or more additional carriers, diluents, and/or excipients. The composition also (or alternatively) may comprise one or more additional active ingredients. For example, such a composition may comprise more than one salt of the compound of Formula I. The composition also may, for example, alternatively or additionally comprise one or more active ingredients other than the compound of Formula I or a salt thereof.

This invention also is directed, in part, to a kit comprising the compound of Formula I or a salt thereof.

This invention also is directed, in part, to the compound of Formula I or a pharmaceutically acceptable salt thereof for use as a medicament.

This invention also is directed, in part, to the use of the compound of Formula I or a pharmaceutically acceptable salt thereof for making a pharmaceutical composition (or "medicament"). In general, such a composition additionally comprises a pharmaceutically acceptable carrier, diluent, or excipient. The composition may further comprise one or more other ingredients. For example, the composition may further comprise one or more additional carriers, diluents, and/or excipients. The composition also (or alternatively) may comprise one or more additional active ingredients. For example, such a composition may comprise more than one salt of the compound of Formula I. The composition also may, for example, alternatively or additionally comprise one or more active ingredients other than the compound of Formula I or a salt thereof.

In some embodiments, the medicament is useful for treating a condition associated with P2X3 activity (particularly excessive activity) in an animal (e.g., a human).

In some embodiments, the medicament is useful for treating a condition associated with P2X2/3 activity (particularly excessive activity) in an animal (e.g., a human).

In some embodiments, the medicament is useful for treating pain in an animal (e.g., a human).

In some embodiments, the medicament is useful for treating a urinary tract disorder in an animal (e.g., a human).

This invention also is directed, in part, to methods for treating a disorder in an animal (e.g., a human) in need of such treatment. These methods comprise administering to the animal the compound of Formula I or pharmaceutically acceptable salt thereof. Such methods encompass the administration of the compound of Formula I or pharmaceutically acceptable salt thereof alone. They also encompass administering other ingredients as well. For example, the compound of Formula I or pharmaceutically acceptable salt thereof will typically be administered as part of a pharmaceutical composition that also comprises one or more carriers, diluents, or excipients. The compound of Formula I or pharmaceutically acceptable salt thereof also may be administered with one or more additional active ingredients. For example, more than one pharmaceutically acceptable salt of the compound of formula I may be administered. Alternatively or additionally, one or more active ingredients other than the compound of Formula I or pharmaceutically acceptable salt thereof may be administered.

In some embodiments, the disorder comprises a disorder associated with P2X3 activity (particularly excessive activity).

In some embodiments, the disorder comprises a disorder associated with P2X2/3 activity (particularly excessive activity).

In some embodiments the disorder comprises pain.

In some embodiments, the disorder comprises a urinary tract disorder.

In general, when the compound of Formula I or a salt thereof is administered as the only active ingredient to treat a targeted disorder, the administered amount of the compound of Formula I or pharmaceutically acceptable salt thereof is therapeutically effective to treat the targeted disorder in the animal. When, in contrast, the compound of Formula I or pharmaceutically acceptable salt thereof is administered in combination with one or more other active ingredients, the amount of the compound of Formula I or a salt thereof and the amount(s) of the other active ingredient(s) are, together, therapeutically effective to treat the targeted disorder in the mammal.

Further benefits of Applicants' invention will be apparent to one skilled in the art from reading this specification.

DESCRIPTION OF ILLUSTRATIVE EMBODIMENTS

This description of illustrative embodiments is intended only to acquaint others skilled in the art with Applicants' invention, its principles, and its practical application so that others skilled in the art may adapt and apply the invention in its numerous forms, as they may be best suited to the requirements of a particular use. This description and its specific examples, while indicating embodiments of this invention, are intended for purposes of illustration only. This invention, therefore, is not limited to the illustrative embodiments described in this specification, and may be variously modified.

As noted above, this invention is directed, in part, to the compound of formula I or a salt thereof. Formula I corresponds to:

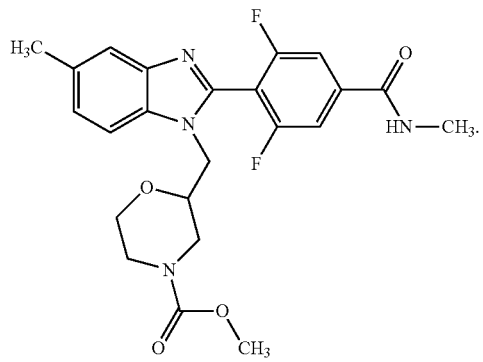

This compound comprises a chiral carbon. Formula I is intended to encompass either chiral isomer corresponding to the structure, as well as any mixture of chiral isomers. A mixture of such isomers may, for example, be a racemic mixture, i.e., a mixture wherein about 50% of the compound is in the form of the S isomer, and about 50% of the mixture is in the form of the R isomer. The S enantiomer (i.e., (S)-methyl 2-((2-(2,6-difluoro-4-(methylcarbamoyl)phenyl)-5-methyl-1H-benzo[d]imidazol-1-yl)methyl)morpholine-4-carboxylate) corresponds in structure to Formula (II):

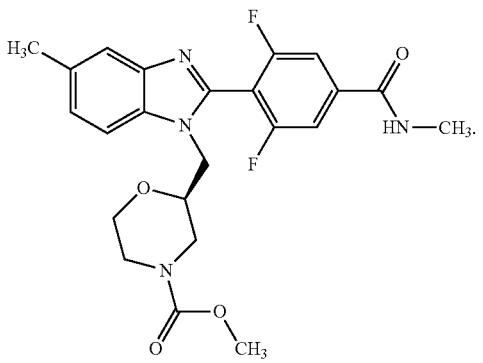

And the R enantiomer (i.e., (R)-methyl 2-((2-(2,6-difluoro-4-(methylcarbamoyl)phenyl)-5-methyl-1H-benzo[d]imidazol-1-yl)methyl)morpholine-4-carboxylate) corresponds in structure to Formula (III):

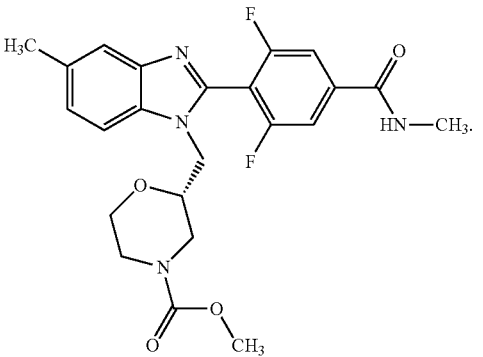

In some embodiments, a single chiral isomer of Formula (I) is obtained by isolating it from a mixture of isomers (e.g., a racemate) using, for example, chiral chromatographic separation. In other embodiments, a single chiral isomer is obtained through direct synthesis from, for example, a chiral starting material. The latter is illustrated in the Examples below.

In each of Formulas II and III, the direction of one of the chiral carbon's substituents is depicted with a dark wedge or hashed wedge. The substituent pointing in the opposite direction is hydrogen. This notation is consistent with conventional organic chemistry nomenclature rules. Thus, Formula II can alternatively be depicted as follows in Formula II-1:

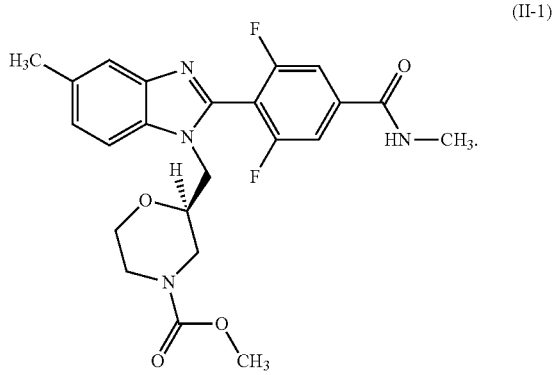 [SMILES: CNC(=O)c1cc(F)c(-c2nc3cc(C)ccc3n2C[C@H]2CN(C(=O)OC)CCO2)c(F)c1]

(II-1)

Similarly, Formula III can alternatively be depicted as follows in Formula III-1:

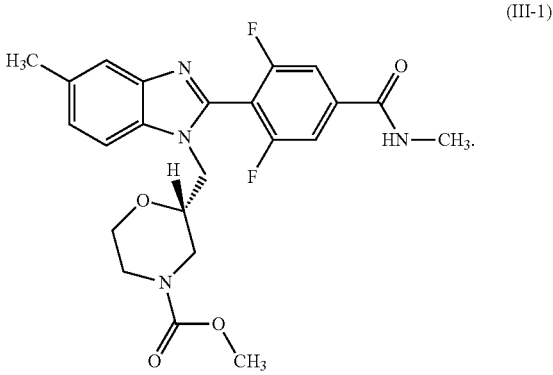 [SMILES: CNC(=O)c1cc(F)c(-c2nc3cc(C)ccc3n2C[C@@H]2CN(C(=O)OC)CCO2)c(F)c1]

(III-1)

Contemplated salts of the compound of Formula I include both acid addition salts and base addition salts. A salt may be advantageous due to one or more of its chemical or physical properties, such as stability in differing temperatures and humidities, or a desirable solubility in water, oil, or other solvent. In some instances, a salt may be used to aid in the isolation or purification of the compound. In some embodiments (particularly where the salt is intended for administration to an animal, or is a reagent for use in making a compound or salt intended for administration to an animal), the salt is pharmaceutically acceptable.

In general, an acid addition salt can be prepared using various inorganic or organic acids. Such salts can typically be formed by, for example, mixing the compound with an acid (e.g., a stoichiometric amount of acid) using various methods known in the art. This mixing may occur in water, an organic solvent (e.g., ether, ethyl acetate, ethanol, isopropanol, or acetonitrile), or an aqueous/organic mixture. Examples of inorganic acids that typically may be used to form acid addition salts include hydrochloric, hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some embodiments, the salt comprises a hydrochloride, hydrobromide, phosphate, acetate, fumarate, maleate, tartrate, citrate, methanesulphonate, or p-toluenesulphonate salt.

The compound of Formula I and salts thereof are intended to encompass any tautomer that may form. A "tautomer" is any other structural isomer that exists in equilibrium resulting from the migration of a hydrogen atom, e.g., amide-imidic acid tautomerism.

It is contemplated that an amine of the compound of Formula I or a salt thereof may form an N-oxide. Such an N-oxide is intended to be encompassed by the compound of formula I and salts thereof. An N-oxide can generally be formed by treating an amine with an oxidizing agent, such as hydrogen peroxide or a per-acid (e.g., a peroxycarboxylic acid). See, e.g., Advanced Organic Chemistry, by Jerry March, 4$^{th}$ Edition, Wiley Interscience. N-oxides also can be made by reacting the amine with m-chloroperoxybenzoic acid (MCPBA), for example, in an inert solvent, such as dichloromethane. See L. W. Deady, *Syn. Comm.*, 7, pp. 509-514 (1977).

It is contemplated that the compound of Formula I or a salt thereof could form isolatable atropisomer in certain solvents at certain temperatures. The compound of formula I and salts thereof are intended to encompass any such atropisomers. Atropisomers can generally be isolated using, for example, chiral LC.

The compound of Formula I and salts thereof are intended to encompass any isotopically-labeled (or "radio-labeled") derivatives of the compound of Formula I or a salt thereof. Such a derivative is a derivative of the compound of Formula I or a salt thereof wherein one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{13}$N, $^{15}$N, $^{15}$O, $^{17}$O, $^{18}$O, and $^{18}$F. The radionuclide that is used will depend on the specific application of that radio-labeled derivative. For example, for in vitro receptor labeling and competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

The compound of Formula I and salts thereof are intended to encompass all solid state forms of the compound of Formula I and salts thereof. The compound of Formula I and salts thereof also are intended to encompass all solvated (e.g., hydrated) and unsolvated forms of the compound of Formula I and salts thereof.

The compound of Formula I and salts thereof also are intended to encompass coupling partners in which the compound of Formula I or a salt thereof is linked to a coupling partner by, for example, being chemically coupled to the compound or salt or physically associated with it. Examples of coupling partners include a label or reporter molecule, a supporting substrate, a carrier or transport molecule, an effector, a drug, an antibody, or an inhibitor. Coupling partners can be covalently linked to the compound of Formula I or a salt thereof via an appropriate functional group on the compound, such as a hydroxyl, carboxyl, or amino group. Other derivatives include formulating the compound of Formula I or a salt thereof with liposomes.

This invention provides, in part, methods to treat various disorders in animals, particularly mammals. Mammals include, for example, humans. Mammals also include, for example, companion animals (e.g., dogs, cats, and horses), livestock animals (e.g., cattle and swine); lab animals (e.g., mice and rats); and wild, zoo, and circus animals (e.g., bears, lions, tigers, apes, and monkeys).

As shown below in Example 6, the chiral isomers of the compound of Formula I have been observed to modulate, and, in particular, act as antagonists against, P2X3. Accordingly, it is believed that the compound of Formula I and salts thereof can be used to modulate P2X3 and/or P2X2/3 to treat various conditions mediated by (or otherwise associated with) P2X3 and/or P2X2/3. It is believed that the compound of Formula I and salts thereof exhibit one or more of the following characteristics: desirable potency, desirable efficacy, desirable stability on the shelf, desirable tolerability for a range of patients, and desirable safety.

It is believed that the compound of Formula I or a salt thereof may be used to treat, for example, pain. Such pain may be, for example, chronic pain, neuropathic pain, acute pain, back pain, cancer pain, pain caused by rheumatoid arthritis, migraine, and visceral pain.

It also is contemplated that the compound of Formula I or a salt thereof may be used to treat a urinary tract disorder. Such disorders include, for example, over-active bladder (also known as urinary incontinence), pelvic hypersensitivity, and urethritis.

It also is contemplated that the compound of Formula I or a salt thereof may be used to treat a gastrointestinal disorder. Such disorders include, for example, constipation and functional gastrointestinal disorders (e.g., irritable bowel syndrome or functional dyspepsia).

It also is contemplated that the compound of Formula I or a salt thereof may be used to treat cancer.

It also is contemplated that the compound of Formula I or a salt thereof may be used to treat a cardiovascular disorder or for cardioprotection following myocardial infarction.

It also is contemplated that the compound of Formula I or a salt thereof may be useful as an immunomodulator, especially for treating an autoimmune disease (e.g., arthritis); for a skin graft, organ transplant, or similar surgical need; for a collagen disease; for an allergy; or as an anti-tumor or anti-viral agent.

It also is contemplated that the compound of Formula I or a salt thereof may be used to treat multiple sclerosis, Parkinson's disease, and Huntington's chorea.

It also is contemplated that the compound of Formula I or a salt thereof may be useful to treat depression, anxiety, a stress-related disorder (e.g., a post-traumatic stress disorder, panic disorder, social phobia, or obsessive compulsive disorder), premature ejaculation, a mental illness, traumatic brain injury, stroke, Alzheimer's disease, spinal injury, drug addiction (e.g., treatment of alcohol, nicotine, opioid, or other drug abuse), or a disorder of the sympathetic nervous system (e.g., hypertension).

It also is contemplated that the compound of Formula I or a salt thereof may be used to treat diarrhea.

It also is contemplated that the compound of Formula I or a salt thereof may be useful to treat a pulmonary disorder, such as, for example, a cough or lung edema.

It also is contemplated that the compound of Formula I or a salt thereof may be used to treat, for example, a disease in which degeneration or dysfunction of cannabinoid receptors is present or implicated in that paradigm. This may, for example, involve the use of an isotopically-labeled version of the compound of Formula I or a salt thereof in a diagnostic technique and imaging application, such as positron emission tomography (PET).

It is contemplated that the compound of Formula I or a pharmaceutically acceptable salt thereof may be administered orally, buccally, vaginally, rectally, via inhalation, via insufflation, intranasally, sublingually, topically, or parenterally (e.g., intramuscularly, subcutaneously, intraperitoneally, intrathoracially, intravenously, epidurally, intrathecally, intracerebroventricularly, or by injection into the joints).

In some embodiments, the compound of Formula I or a salt thereof is administered orally.

In some embodiments, the compound of Formula I or a salt thereof is administered intravenously.

In some embodiments, the compound of Formula I or a salt thereof is administered intramuscularly.

In some embodiments, the compound of Formula I or a salt thereof is used to make a medicament (i.e., a pharmaceutical composition). In general, the pharmaceutical composition comprises a therapeutically effective amount of the compound or salt. Pharmaceutical compositions comprising the compound of Formula I or a salt thereof can vary widely. Although it is contemplated that the compound of Formula I or a salt thereof could be administered by itself (i.e., without any other active or inactive ingredient), the pharmaceutical composition normally will instead comprise one or more additional active ingredients and/or inert ingredients. The inert ingredients present in the pharmaceutical compositions of this invention are sometimes collectively referred to as "carriers, diluents, and excipients." Methods for making pharmaceutical compositions and the use of carriers, diluents, and excipients are well known in the art. See, e.g., for example, *Remington's Pharmaceutical Sciences*, Mack Publishing Company, Easton, Pa., 15th Edition, 1975.

Pharmaceutical compositions comprising the compound of Formula I or pharmaceutically acceptable salt thereof can vary widely. For example, it is contemplated that the compositions may be formulated for a variety of suitable routes and means of administration, including oral, rectal, nasal, topical, buccal, sublingual, vaginal, inhalation, insufflation, or parenteral administration. It is contemplated that such compositions may, for example, be in the form of solids, aqueous or oily solutions, suspensions, emulsions, creams, ointments, mists, gels, nasal sprays, suppositories, finely divided powders, and aerosols or nebulisers for inhalation. In some embodiments, the composition comprises a solid or liquid dosage form that may be administered orally.

Solid form compositions may include, for example, powders, tablets, dispersible granules, capsules, cachets, and suppositories. A solid carrier may comprise one or more substances. Such substances are generally inert. A carrier also may act as, for example, a diluent, flavoring agent, solubilizer, lubricant, preservative, stabilizer, suspending agent, binder, or disintegrating agent. It also may act as, for example, an encapsulating material. Examples of often suitable carriers include pharmaceutical grade mannitol, lactose, magnesium carbonate, magnesium stearate, talc, lactose, sugar (e.g., glucose and sucrose), pectin, dextrin, starch, tragacanth, cellulose, cellulose derivatives (e.g., methyl cellulose and sodium carboxymethyl cellulose), sodium saccharin, low-melting wax, and cocoa butter.

In powders, the carrier is typically a finely divided solid, which is in a mixture with the finely divided active component. In tablets, the active component is typically mixed with the carrier having the desirable binding properties in suitable proportions and compacted into the desired shape and size.

For preparing suppository compositions, a low-melting wax (e.g., a mixture of fatty acid glycerides and cocoa butter) is typically first melted, followed by dispersing the active ingredient therein by, for example, stirring. The molten homogeneous mixture is then poured into convenient-sized molds and allowed to cool and solidify. Examples of non-irritating excipients that may be present in suppository compositions include, for example, cocoa butter, glycerinated gelatin, hydrogenated vegetable oils, mixtures of polyethylene glycols of various molecular weights, and fatty acid esters of polyethylene glycol.

Liquid compositions can be prepared by, for example, dissolving or dispersing the compound of Formula I or a salt thereof in a carrier, such as, for example, water, water/propylene glycol solutions, saline aqueous dextrose, glycerol, or ethanol. In some embodiments, aqueous solutions for oral administration can be prepared by dissolving the compound of Formula I or a salt thereof in water with a solubilizer (e.g., a polyethylene glycol). Colorants, flavoring agents, stabilizers, and thickening agents, for example, also may be added. In some embodiments, aqueous suspensions for oral use can be made by dispersing the compound of Formula I or a salt thereof in a finely divided form in water, together with a viscous material, such as, for example, one or more natural synthetic gums, resins, methyl cellulose, sodium carboxymethyl cellulose, or other suspending agents. If desired, the liquid composition also may contain other non-toxic auxiliary inert ingredients, such as, for example, wetting or emulsifying agents, pH buffering agents and the like, for example, sodium acetate, sorbitan monolaurate, triethanolamine sodium acetate, sorbitan monolaurate, triethanolamine oleate, etc. Such compositions also may contain other ingredients, such as, for example, one or more pharmaceutical adjuvants.

In some embodiments, the pharmaceutical composition comprises from about 0.05% to about 99% (by weight) of the compound of Formula I or a salt thereof. In some such embodiments, for example, the pharmaceutical composition comprises from about 0.10% to about 50% (by weight) of the compound of Formula I or a salt thereof.

In some embodiments, the pharmaceutical composition comprises from about 0.05% to about 99% (by weight) of the S isomer (i.e., the compound of Formula II) or a salt thereof. In some such embodiments, for example, the pharmaceutical composition comprises from about 0.10% to about 50% (by weight) of the S isomer or a salt(s) thereof.

In some embodiments, the pharmaceutical composition comprises from about 0.05% to about 99% (by weight) of the R isomer (i.e., the compound of Formula III) or a salt thereof. In some such embodiments, for example, the pharmaceutical composition comprises from about 0.10% to about 50% (by weight) of the R isomer or a salt(s) thereof.

In some embodiments, a composition is prepared wherein at least about 50% (by weight) of the composition is the S isomer or a salt(s) thereof. In some such embodiments, the concentration is greater than about 70% (by weight), greater than about 85% (by weight), greater than about 90% (by weight), greater than about 95% (by weight), greater than about 98% (by weight), greater than about 99% (by weight), or greater than about 99.5% (by weight). Such a composition may be, for example, a pharmaceutical composition or a composition used in the preparation of a pharmaceutical composition (e.g., a composition that is, for example, dispersed into a carrier, diluent, or excipient before being administered).

In some embodiments, a composition is prepared wherein at least about 50% (by weight) of the composition is the R isomer or a salt(s) thereof. In some such embodiments, the concentration is greater than about 70% (by weight), greater than about 85% (by weight), greater than about 90% (by weight), greater than about 95% (by weight), greater than about 98% (by weight), greater than about 99% (by weight), or greater than about 99.5% (by weight). Such a composition may be, for example, a pharmaceutical composition or a composition used in the preparation of a pharmaceutical composition (e.g., a composition that is, for example, dispersed into a carrier, diluent, or excipient before being administered).

In some embodiments, the molar ratio of the S isomer (or salt(s) thereof) to the R isomer (or salt(s) thereof) in a pharmaceutical composition of this invention is about 1:1, i.e., the composition comprises a racemic mixture.

In some embodiments, the molar ratio of the S isomer (or salt(s) thereof) to the R isomer of Formula I (or salt(s) thereof) in a pharmaceutical composition of this invention is greater than about 70:30. In some such embodiments, the ratio is greater than about 85:15, greater than about 90:10, greater than about 95:5, greater than about 98:2, greater than about 99:1, or greater than about 99.5:0.5.

In some embodiments, the molar ratio of the R isomer (or salt(s) thereof) to the S isomer of Formula I (or salt(s) thereof) in a pharmaceutical composition of this invention is greater than about 70:30. In some such embodiments, the ratio is greater than about 85:15, greater than about 90:10, greater than about 95:5, greater than about 98:2, greater than about 99:1, or greater than about 99.5:0.5.

When the compound of Formula I or a salt thereof is administered as a sole therapy for treating a disorder, a "therapeutically effective amount" is an amount sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder.

The optimum dosage and frequency of administration will depend on the particular condition being treated and its severity; the species of the patient; the age, size and weight, diet, and general physical condition of the particular patient; brain/body weight ratio; other medication the patient may be taking; the route of administration; the formulation; and various other factors known to physicians (in the context of human patients), veterinarians (in the context of non-human patients), and others skilled in the art.

It is contemplated that in some embodiments, the optimum amount of the compound of Formula I or a salt thereof is at least about 10 pg/kg of body weight per day. In some embodiments, the optimum amount is no greater than about 100 mg/kg of body weight per day. In some embodiments, the optimum amount is from about 10 pg/kg to about 100 mg/kg of body weight per day. In some embodiments, the optimum amount is from about 0.01 to about 10 mg/kg of body weight per day. In some embodiments, the optimum amount is from about 2 to about 20 mg/kg of body weight per day. In some embodiments, the optimum amount is from about 2.5 to about 8 mg/kg of body weight per day. In still other embodiments, the optimum amount is from about 0.8 to about 2.5 mg/kg of body weight per day.

It is contemplated that the pharmaceutical compositions can be in one or more unit dosage forms. Accordingly, the composition may be divided into unit doses containing appropriate quantities of the active component. The unit dosage form can be, for example, a capsule, cachet, or tablet itself, or it can be the appropriate number of any of these in packaged forms. The unit dosage form alternatively can be a packaged preparation in which the package contains discrete quantities of the composition, such as, for example, packeted tablets, capsules, or powders in vials or ampoules. Unit dosage forms may be prepared by, for example, various methods well known in the art of pharmacy.

It is contemplated that a dosage can be given once daily or in divided doses, such as, for example, from 2 to 4 times per day. In some embodiments, the dose is conventionally formulated in an oral dosage form by compounding from about 5 to about 250 mg per unit of dosage with, for example, one or more inert or active ingredients using accepted pharmaceutical practices.

In some embodiments, the compound of Formula I or a salt thereof is administered concurrently, simultaneously, sequentially, or separately with one or more other pharmaceutically active compounds. In some such embodiments, the other pharmaceutically active compound(s) is/are selected from the following:

(i) Antidepressants, which are contemplated to include, for example, one or more of agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, mirtazepine, nortriptyline, nefazodone, paroxetine, phenelzine, protriptyline, ramelteon, reboxetine, robalzotan, selegiline, sertraline, sibutramine, thionisoxetine, tranylcypromaine, trazodone, trimipramine, venlafaxine and equivalents and pharmaceutically active isomer(s) and metabolite(s) thereof.

(ii) Antipsychotics, which are contemplated to include, for example, one or more of quetiapine and pharmaceutically active isomer(s) and metabolite(s) thereof; and amisulpride, aripiprazole, asenapine, benzisoxidil, bifeprunox, carbamazepine, clozapine, chlorpromazine, debenzapine, dibenzapine, divalproex, droperidol, duloxetine, eszopiclone, fluphenazine, haloperidol, iloperidone, lamotrigine, lithium, loxapine, mesoridazine, molindone, olanzapine, paliperidone, perlapine, perphenazine, phenothiazine, phenylbutylpiperidine, pimozide, prochlorperazine, risperidone, sertindole, sulpiride, suproclone, suriclone, thioridazine, thiothixene, trifluoperazine, trimetozine, valproate, valproic acid, zopiclone, zotepine, ziprasidone, and equivalents thereof.

(iii) Anxiolytics, which are contemplated to include, for example, one or more of alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, suriclone, tracazolate, trepipam, temazepam, triazolam, uldazepam, zolazepam and equivalents and pharmaceutically active isomer(s) and metabolite(s) thereof.

(iv) Anticonvulsants, which are contemplated to include, for example, one or more of carbamazepine, oxcarbazepine, valproate, lamotrigine, gabapentin, topiramate, phenyloin, ethoxuximide, and equivalents and pharmaceutically active isomer(s) and metabolite(s) thereof.

(v) Alzheimer's therapies, which are contemplated to include, for example, donepezil, galantamine, memantine, rivastigmine, tacrine and equivalents and pharmaceutically active isomer(s) and metabolite(s) thereof.

(vi) Parkinson's therapies and agents for the treatment of extrapyramidal symtpoms, which are contemplated to include, for example, one or more of levodopa, carbidopa, amantadine, pramipexole, ropinirole, pergolide, cabergoline, apomorphine, bromocriptine, MAOB inhibitors (e.g., selegine and rasagiline), COMT inhibitors (e.g., entacapone and tolcapone), alpha-2 inhibitors, anticholinergics (e.g., benztropine, biperiden, orphenadrine, procyclidine, and trihexyphenidyl), dopamine reuptake inhibitors, NMDA antagonists, Nicotine agonists, Dopamine agonists, and inhibitors of neuronal nitric oxide synthase, and equivalents and pharmaceutically active isomer(s) and metabolite(s) thereof.

(vii) Stroke therapies, which are contemplated to include, for example, one or more of abciximab, activase, disufenton sodium, citicoline, crobenetine, desmoteplase, repinotan, traxoprodil, and equivalents and pharmaceutically active isomer(s) and metabolite(s) thereof.

(viii) Urinary incontinence therapies, which are contemplated to include, for example, one or more of darafenacin, dicyclomine, falvoxate, imipramine, desipramine, oxybutynin, propiverine, propanthedine, robalzotan, solifenacin, alfazosin, doxazosin, terazosin, tolterodine, and equivalents and pharmaceutically active isomer(s) and metabolite(s) thereof.

(ix) Insomnia therapies, which are contemplated to include, for example, one or more of allobarbital, alonimid, amobarbital, benzoctamine, butabarbital, capuride, chloral, cloperidone, clorethate, dexclamol, estazolam, eszopicline, ethchlorvynol, etomidate, flurazepam, glutethimide, halazepam, hydroxyzine, mecloqualone, melatonin, mephobarbital, methaqualone, midaflur, midazolam, nisobamate, pagoclone, pentobarbital, perlapine, phenobarbital, propofol, quazepam, ramelteon, roletamide, suproclone, temazepam, triazolam, triclofos, secobarbital, zaleplon, zolpidem, zopiclone, and equivalents and pharmaceutically active isomer(s) and metabolite(s) thereof.

(x) Mood stabilizers, which are contemplated to include, for example, one or more of carbamazepine, divalproex, gabapentin, lamotrigine, lithium, olanzapine, quetiapine, valproate, valproic acid, verapamil, and equivalents and pharmaceutically active isomer(s) and metabolite(s) thereof.

(xi) Medications for treating obesity, such as, for example, orlistat, sibutramine, rimonabant, and equivalents and pharmaceutically active isomer(s) and metabolite(s) thereof.

(xii) Agents for treating ADHD, which are contemplated to include, for example, one or more of amphetamine, methamphetamine, dextroamphetamine, atomoxetine, methylphenidate, dexmethylphenidate, modafinil, and equivalents and pharmaceutically active isomer(s) and metabolite(s) thereof.
(xiii) Agents used to treat substance abuse disorders, dependence, and withdrawal, which are contemplated to include, for example, one or more of nicotine replacement therapies (e.g., gum, patches, and nasal spray); nicotinergic receptor agonists, partial agonists, and antagonists, (e.g., varenicline); acomprosate; bupropion; clonidine; disulfuram; methadone; naloxone; naltrexone; and equivalents and pharmaceutically active isomer(s) and metabolite(s) thereof.

In some embodiments, the other pharmaceutically active ingredient(s) comprises an atypical antipsychotic agent. Atypical antipsychotic agents include, for example, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON), and olanzapine/fluoxetine (marketed as SYMBYAX).

In some embodiments, the other pharmaceutically active ingredient(s) comprises a selective serotonin reuptake inhibitor (or "serotonin-specific reuptake inhibitor" or SSRI"). Such agents include, for example, fluoxetine (marketed as, for example, PROZAC), paroxetine (marketed as, for example, PAXIL), citalopram (marketed as, for example, CELEXA), dapoxetine, mesembrine, excitalopram (marketed as, for example, LEXAPRO), fluvoxamine (marketed as, for example, LUVOX), zimelidine (marketed as, for example, ZELMID), and sertraline (marketed as, for example, ZOLOFT).

In some embodiments, the compound of Formula I or a salt thereof is administered as part of a combination therapy with radiotherapy.

In some embodiments, the compound of Formula I or a salt thereof is administered as a combination therapy with chemotherapy. Such chemotherapy may include one or more of the following categories of anti-tumour agents:
(i) Antiproliferative/antineoplastic drugs, which are contemplated to include, for example, alkylating agents, such as cis-platin, oxaliplatin, carboplatin, cyclophosphamide, nitrogen mustard, melphalan, chlorambucil, busulphan, temozolamide, and nitrosoureas; antimetabolites, such as gemcitabine and antifolates (e.g., fluoropyrimidines (like 5-fluorouracil and tegafur), raltitrexed, methotrexate, cytosine arabinoside, and hydroxyurea); antitumour antibiotics, such as anthracyclines (e.g., adriamycin, bleomycin, doxorubicin, daunomycin, epirubicin, idarubicin, mitomycin-C, dactinomycin and mithramycin); antimitotic agents, such as vinca alkaloids (e.g., vincristine, vinblastine, vindesine, and vinorelbine), taxoids (e.g., TAXOL and TAXOTERE), and polokinase inhibitors; and topoisomerase inhibitors, such as epipodophyllotoxins (e.g., etoposide and teniposide), amsacrine, topotecan, and camptothecin.
(ii) Cytostatic agents, which are contemplated to include, for example, antioestrogens, such as tamoxifen, fulvestrant, toremifene, raloxifene, droloxifene, and iodoxyfene; antiandrogens, such as bicalutamide, flutamide, nilutamide, and cyproterone acetate; LHRH antagonists; LHRH agonists, such as goserelin, leuprorelin, and buserelin; progestogens, such as megestrol acetate; aromatase inhibitors, such as anastrozole, letrozole, vorazole, and exemestane; and 5α-reductase inhibitors, such as finasteride.
(iii) Anti-invasion agents, which are contemplated to include, for example, c-Src kinase family inhibitors, such as 4-(6-chloro-2,3-methylenedioxyanilino)-7-[2-(4-methylpiperazin-1-yl)ethoxy]-5-tetrahydropyran-4-yloxyquinazoline (AZD0530, Int'l Patent Appl. Publ. WO01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825, J. Med. Chem., vol. 47, pp. 6658-6661 (2004)), and bosutinib (SKI-606); metalloproteinase inhibitors, such as marimastat; inhibitors of urokinase plasminogen activator receptor function; and antibodies to heparanase.
(iv) Inhibitors of growth factor function, which are contemplated to include, for example, growth factor antibodies; growth factor receptor antibodies, such as the anti-erbB2 antibody trastuzumab (HERCEPTIN), the anti-EGFR antibody panitumumab, the anti-erbB 1 antibody cetuximab (ERBITUX, C225), and growth factor or growth factor receptor antibodies disclosed by Stern et al., Critical reviews in oncology/haematology, vol. 54, pp. 11-29 (2005); tyrosine kinase inhibitors, such as inhibitors of the epidermal growth factor family (e.g., EGFR family tyrosine kinase inhibitors like N-(3-chloro-4-fluorophenyl)-7-methoxy-6-(3-morpholinopropoxy)quinazolin-4-amine (gefitinib, ZD1839), N-(3-ethynylphenyl)-6,7-bis (2-methoxyethoxy)quinazolin-4-amine (erlotinib, OSI-774), and 6-acrylamido-N-(3-chloro-4-fluorophenyl)-7-(3-morpholinopropoxy)-quinazolin-4-amine (CI 1033)) and erbB2 tyrosine kinase inhibitors (e.g., lapatinib); inhibitors of the hepatocyte growth factor family; inhibitors of the insulin growth factor family; inhibitors of the platelet-derived growth factor family, such as imatinib and nilotinib (AMN107); inhibitors of serine/threonine kinases, such as Ras/Raf signalling inhibitors (e.g., farnesyl transferase inhibitors like sorafenib (BAY 43-9006), tipifarnib (R115777), and lonafarnib (SCH66336)); inhibitors of cell signalling through MEK and/or AKT kinases; c-kit inhibitors; abl kinase inhibitors, PI3 kinase inhibitors; Plt3 kinase inhibitors; CSF-1R kinase inhibitors; IGF receptor (insulin-like growth factor) kinase inhibitors); aurora kinase inhibitors, such as AZD1152, PH739358, VX-680, MLN8054, R763, MP235, MP529, VX-528, and AX39459; and cyclin dependent kinase inhibitors, such as CDK2 and CDK4 inhibitors.
(v) Antiangiogenic agents, which are contemplated to include, for example, those that inhibit the effects of vascular endothelial growth factor, such as anti-vascular endothelial cell growth factor antibody bevacizumab (AVASTIN) and a VEGF receptor tyrosine kinase inhibitor (e.g., vandetanib (ZD6474), vatalanib (PTK787), sunitinib (SU11248), axitinib (AG-013736), pazopanib (GW 786034), and 4-(4-fluoro-2-methylindol-5-yloxy)-6-methoxy-7-(3-pyrrolidin-1-ylpropoxy)quinazoline (AZD2171, Example 240 in Intl. Patent Appl. Publ. WO 00/47212); compounds disclosed in Int'l Patent Appl. Publ. WO97/22596, WO 97/30035, WO 97/32856, and WO 98/13354; and compounds that work by other mechanisms, such as linomide, inhibitors of integrin αvβ3 function, and angiostatin.
(vi) Vascular damaging agents, which are contemplated to include, for example, combretastatin A4 and compounds disclosed in Int'l Patent Appl. Publ. WO 99/02166, WO 00/40529, WO 00/41669, WO 01/92224, WO 02/04434, and WO 02/08213.
(vii) Endothelin receptor antagonists, which are contemplated to include, for example, zibotentan (ZD4054) and atrasentan.
(viii) Antisense therapies, which are contemplated to include, for example, those that are directed to the targets listed above, such as ISIS 2503 (an anti-ras antisense).

(ix) Gene therapy approaches, which are contempated to include, for example, approaches to replace aberrant genes, such as aberrant p53, BRCA1, or BRCA2; GDEPT (gene-directed enzyme pro-drug therapy) approaches, such as those using cytosine deaminase, thymidine kinase, or a bacterial nitroreductase enzyme; and approaches to increase patient tolerance to chemotherapy or radiotherapy, such as multi-drug resistance gene therapy.

(x) Immunotherapy approaches, which are contemplated to include, for example, ex-vivo and in-vivo approaches to increase the immunogenicity of patient tumour cells, such as transfection with cytokines (e.g., interleukin 2, interleukin 4, or granulocyte-macrophage colony stimulating factor); approaches to decrease T-cell anergy; approaches using transfected immune cells, such as cytokine-transfected dendritic cells; approaches using cytokine-transfected tumour cell lines; and approaches using anti-idiotypic antibodies.

It also is contemplated that the compound of Formula I or a salt thereof may be useful as an analgesic agent for use during general anesthesia or monitored anesthesia care. Combinations of agents with different properties are often used to achieve a balance of effects needed to maintain the anesthetic state (e.g., amnesia, analgesia, muscle relaxation, and sedation). Such a combination may include, for example, one or more inhaled anesthetics, hypnotics, anxiolytics, neuromuscular blockers, and/or opioids.

In some embodiments in which a combination therapy is used, the amount of the compound of Formula I or a salt thereof and the amount of the other pharmaceutically active agent(s) are, when combined, therapeutically effective to treat a targeted disorder in the animal patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder. Typically, such amounts may be determined by one skilled in the art by, for example, starting with the dosage range described in this patent for the compound of Formula I or a salt thereof and an approved or otherwise published dosage range(s) of the other pharmaceutically active compound(s).

When used in a combination therapy, it is contemplated that the compound of Formula I or a salt thereof and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

This invention also is directed, in part, to a kit comprising the compound of Formula I or a salt thereof. In some embodiments, the kit further comprises one or more additional components, such as, for example: (a) an apparatus for administering the compound of Formula I or a salt thereof; (b) instructions for administering the compound of Formula I or a salt thereof; (c) a carrier, diluent, or excipient (e.g., a resuspending agent); and (d) an additional active ingredient, which may be in the same and/or different dosage forms as the compound of Formula I or salt thereof. In some embodiments (particularly when the kit is intended for use in administering the compound of Formula I or salt thereof to an animal patient), the salt is a pharmaceutically acceptable salt.

EXAMPLES

The following examples are merely illustrative of embodiments of the invention, and not limiting to the remainder of this disclosure in any way.

In some instances in the following examples, compound structures are associated with compound names. In general, such names were generated from the structures using AutoNom 2000 within ISIS/Draw or ChemDraw 9.0.7. AutoNom (Automatic Nomenclature) and ChemDraw contain programs that assign systematic IUPAC (International Union of Pure and Applied Chemistry) chemical names to drawn structures at the press of a button. In some instances, however, the chemical names were manually revised to ensure compliance with IUPAC naming conventions. If there are any differences between a structure and name for a compound, the compound should be identified by the structure unless the context indicates otherwise.

Compound Preparation

Examples 1-5 below illustrate the preparation of the compound of Formula I or a salt thereof and intermediates for making such compounds. It is expected that one skilled in the art of organic synthesis, after reading these examples alone or in combination with the general knowledge in the art, can adapt and apply the methods as desired. The general knowledge in the art includes, for example:

A) Conventional procedures for using protective groups and examples of suitable protective groups, which are described in, for example, *Protective Groups in Organic Synthesis*, T. W. Green, P. G. M. Wuts, Wiley-Interscience, New York (1999).

B) References discussing various organic synthesis reactions, include textbooks of organic chemistry, such as, for example, *Advanced Organic Chemistry, March 4th ed*, McGraw Hill (1992); and *Organic Synthesis*, Smith, McGraw Hill, (1994). They also include, for example, R. C. Larock, *Comprehensive Organic Transformations, 2nd ed.*, Wiley-VCH: New York (1999); F. A. Carey; R. J. Sundberg, *Advanced Organic Chemistry, 2nd ed.*, Plenum Press: New York (1984); L. S. Hegedus, *Transition Metals in the Synthesis of Complex Organic Molecules, 2nd ed.*, University Science Books: Mill Valley, Calif. (1994); L. A. Paquette, Ed., *The Encyclopedia of Reagents for Organic Synthesis*, John Wiley: New York (1994); A. R. Katritzky, O. Meth-Cohn, C W. Rees, Eds., *Comprehensive Organic Functional Group Transformations*, Pergamon Press: Oxford, UK (1995); G. Wilkinson; F. G A. Stone; E. W. Abel, Eds., *Comprehensive Organometallic Chemistry*, Pergamon Press: Oxford, UK (1982); B. M. Trost; I. Fleming, *Comprehensive Organic Synthesis*, Pergamon Press: Oxford, UK (1991); A. R. Katritzky, C W. Rees Eds., *Comprehensive Heterocyclic Chemistry*, Pergamon Press: Oxford, UK (1984); A. R. Katritzky; C W. Rees, E. F. V. Scriven, Eds., *Comprehensive Heterocyclic Chemistry II*, Pergamon Press: Oxford, UK (1996); C. Hansen; P. G. Sammes; J. B. Taylor, Eds., *Comprehensive Medicinal Chemistry*: Pergamon Press: Oxford, UK (1990). In addition, recurring reviews of synthetic methodology and related topics include: Organic Reactions, John Wiley: New York; *Organic Syntheses*; John Wiley: New York; *The Total Synthesis of Natural Products*, John Wiley: New York; *The Organic Chemistry of Drug Synthesis*, John Wiley: New York; *Annual Reports in Organic Synthesis*, Academic Press: San Diego Calif.; and *Methoden der Organischen Chemie* (Houben-Weyl), Thieme: Stuttgart, Germany.

C) References discussing heterocyclic chemistry include, for example, example, *Heterocyclic Chemistry*, J. A. Joule, K. Mills, G. F. Smith, 3rd ed., Cheapman and Hall, p. 189-225 (1995); and *Heterocyclic Chemistry*, T. L. Gilchrist, 2$^{nd}$ ed. Longman Scientific and Technical, p. 248-282 (1992).

D) Databases of synthetic transformations, including Chemical Abstracts, which may be searched using either CAS Online or SciFinder; and Handbuch der Organischen Chemie (Beilstein), which may be searched using SpotFire.

All starting materials in the following compound preparation examples are commercially available or described in the literature. Air and moisture-sensitive liquids and solutions were transferred via syringe or cannula, and introduced into reaction vessels through rubber septa. Commercial grade reagents and solvents were used without further purification. The terms "concentration under reduced pressure" and "evaporated under reduce pressure" or "concentrated in vacuo" refer to use of a Buchi rotary evaporator at approximately 15 mm of Hg.

Microwave heating was performed either on a CEM Discover LabMate or on a Biotage Initiator System at the indicated temperature in the recommended microwave tubes.

Where indicated in the text, column chromatography (flash chromatography) was performed using 32-63 micron, 60 Å, silica gel prepacked cartridges (on a Biotage or ISCO system), or a glass column and air pressure. Preparative HPLC or LCMS (high pH or low pH) was performed using a Waters X-bridge Prep $C_{18}$ OBD (column size: 30×50 mm; particle size: 5 μm; mobile phase A: water 10 mM $NH_4HCO_3$ (pH 10) or water with 0.1% TFA; and mobile phase B: MeCN).

Mass spectra were recorder using either Single-Quad mass spectrometers equipped with an electrospray ion source (ES) operated in a positive or negative ion mode or a Triple-Quad mass spectrometer configured with an atmospheric pressure chemical ionisation (APCI) ion source operated in positive and negative ion mode. The mass spectrometers were scanned between m/z 100-1000 with a scan time of 0.3 sec.

$^1$H NMR spectra were recorded on Varian NMR Spectrometer at 300 MHz, 400 MHz or alternatively on a Bruker Avance 500 NMR Spectrometer at 500 MHz.

Unless otherwise specified, HRMS analyses were performed on an Agilent 1100 HPLC with an Agilent MSD-TOF mass spectrometer and an Agilent 1100 Diode Array Detector using a Zorbax C-18 column (column size: 30×4.6 mm; particle size: 1.8 μm, gradient: 5-95% B in 4.5 min; flow rate: 3.5 mL/min; temperature: 70° C., eluents A: 0.05% TFA in $H_2O$; and eluent B: 0.05% TFA in $CH_3CN$).

Example 1

Preparation of 3,5-difluoro-4-formylbenzoic acid

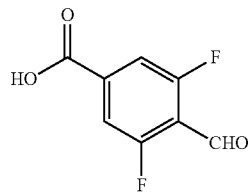

To a solution of 3,5-difluorobenzoic acid (291 g, 1.84 mol) in 2-methyltetrahydrofuran (4.35 L) was added TMEDA (604 mL, 4.03 mol) at room temperature. The resulting solution was cooled to −78° C. Afterward, n-BuLi (2.5 M in hexane) (1.77 L, 4.43 mol) was added drop-wise, during which the temperature of the mixture remained at less than −65° C. The mixture was then stirred at −78° C. for 1.5 hr. Anhydrous MeOCHO (239 mL, 3.88 mol) was added dropwise at a rate that allowed the temperature to be maintained at less than −65° C. The resulting solution was allowed to warm at room temperature, and then maintained a room temperature while being stirred for 18 hr. The mixture was then cooled to 0-5° C., and excess base was quenched with 6M aqueous HCl (2.2 L, 13.2 mol). The phases were then separated, and the aqueous layer was extracted 3 times with 2-methyltetrahydrofuran (3×500 mL). The combined organic phases were washed with saturated brine, dried over $MgSO_4$, filtered, and concentrated under vacuum. The residue was dissolved in ethyl acetate (350 mL) at reflux, and cooled to room temperature. Hexanes (480 mL) were then added, and the resulting mixture was further cooled to −15° C. The solid was collected by filtration, rinsed with hexanes, and dried under mechanical vacuum to form the title compound (122 g, 35%) as a solid. $^1$H NMR (300 MHz, DMSO-$d_6$) δ ppm 7.63-7.70 (m, 2H), 10.23 (s, 1H); MS m/z 187.17 [M+H]$^+$ (ESI).

Example 2

Preparation of 3,5-difluoro-4-formyl-N-methylbenzamide

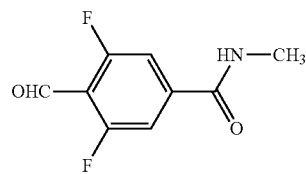

To an ice-cold solution of 3,5-difluoro-4-formylbenzoic acid (120 g, 645 mmol) in dichloromethane (1.5 L) and N,N-dimethylformamide (2.0 g, 27 mmol) was added oxalyl chloride (90 g, 709 mmol) drop-wise at a rate that allowed the mixture to not exceed an internal temperature of 10° C. The resulting mixture was stirred at the same temperature for 0.5 hr, warmed to room temperature, and stirred for an additional 1.5 hr. The solution was then cooled to 0° C., and aqueous methylamine (40%, 168 mL, 1.94 mol) was added drop-wise at a rate that allowed the mixture to not exceed an internal temperature of 7° C. Afterward, the mixture was quenched with aqueous HCl (2M, 335 mL, 670 mmol) and warmed to room temperature. The organic layer was separated, washed with brine (500 mL), dried over $MgSO_4$, filtered, and concentrated under vacuum. The resulting residual solid was taken in MTBE (500 mL), and the resulting mixture was heated to reflux for 0.5 hr, cooled to room temperature, and stirred for 18 hr. Afterward, the mixture was cooled to 0° C., filtered, rinsed with pentane, and dried under vacuum to form the title compound (103 g, 80%) as a solid. $^1$H NMR (300 MHz, CDCl₃) δ ppm 3.03 (d, J=4.86 Hz, 3H), 6.37 (br s, 1H), 7.36-7.42 (m, 2H), 10.36 (s, 1H); MS m/z 200.06 [M+H]⁺ (ESI).

Example 3

Preparation of (S)-methyl 2-((2-(2,6-difluoro-4-(methylcarbamoyl)phenyl)-5-methyl-1H-benzo[d]imidazol-1-yl)methyl)morpholine-4-carboxylate

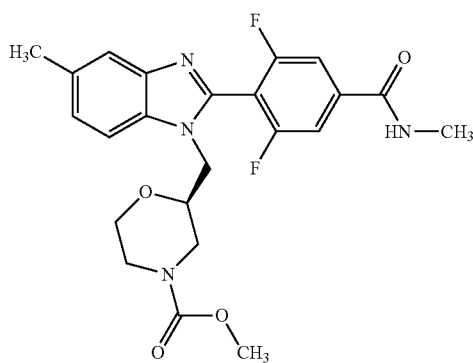

Part A. Preparation of (S)-tert-butyl 2-((1,3-dioxoisoindolin-2-yl)methyl)morpholine-4-carboxylate

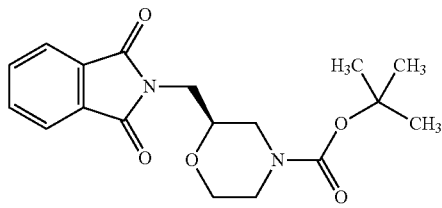 [SMILES: CC(C)(C)OC(=O)N1CCO[C@@H](CN2C(=O)c3ccccc3C2=O)C1]

A mixture of (R)-tert-butyl 2-(hydroxymethyl)morpholine-4-carboxylate (750 g, 3.45 mol) was stirred with triethylamine (577 mL, 4.14 mol) and toluene (6000 mL) at 3° C. under N₂. Methanesulfonyl chloride (321 mL, 4.14 mol) was added over 2.5 hr, keeping the temperature at less than 15° C. When the addition was finished, the temperature was increased to 35° C., and water (2000 mL) was added. The phases were mixed for 10 min and then allowed to settle. The aqueous phase was drawn off and water (1500 mL) was added. The phases were mixed again for 10 min, and then the aqueous phase was removed. Toluene (4000 mL) was added to the vessel, and 2000 mL of distillate was removed under reduced pressure at 50° C. The temperature was then reduced to 20° C., and potassium phthalimide (864 g, 4.66 mol) and tetrabutylammonium bromide (111 g, 0.35 mol) were added. The mixture was stirred at 108° C. for 4 hr, and then cooled to 20° C. Water (1000 mL) and 5% aqueous NaOH (2500 mL) were added. The resulting mixture was stirred for 10 min. The phases were then allowed to settle, and the aqueous phase was removed. Water (2000 mL) was added, and the resulting mixture was stirred for an additional 10 min. The aqueous phase was then removed. A total of 7 L of distillate were removed under reduced pressure at a temperature ranging from 60 to 85° C. The vessel was cooled to 65° C., and heptanes (3000 mL) was added. The temperature was further decreased to 25° C., and the solution was seeded with crystalline sample of the title compound. The mixture was stirred for 1 hr until crystallization was well under way. After adding heptanes (2500 mL), the mixture was cooled to 10° C. and then stirred for an additional 24 hr. Afterward, the mixture was filtered, and the solid was washed with 800 mL of a cold solution of 10% toluene in heptanes and dried under mechanical vacuum oven at 45° C. for 16 hr to produce (S)-tert-butyl 2-((1,3-dioxoisoindolin-2-yl)methyl)morpholine-4-carboxylate (614 g, 51%) as a solid. ¹H NMR (500 MHz, chloroform-d) δ ppm 1.38 (s, 9H), 2.69 (br. s., 1H), 2.92 (br. s., 1H), 3.37 (td, J=11.51, 2.76 Hz, 1H), 3.60 (dd, J=13.75, 4.53 Hz, 1H), 3.63-4.01 (m, 5H), 7.66 (dd, J=5.32, 3.03 Hz, 2H), 7.79 (dd, J=5.04, 3.07 Hz, 2H).

Part B. Preparation of (S)-tert-butyl 2-((2-(2,6-difluoro-4-(methylcarbamoyl)phenyl)-5-methyl-1H-benzo[d]imidazol-1-yl)methyl)morpholine-4-carboxylate

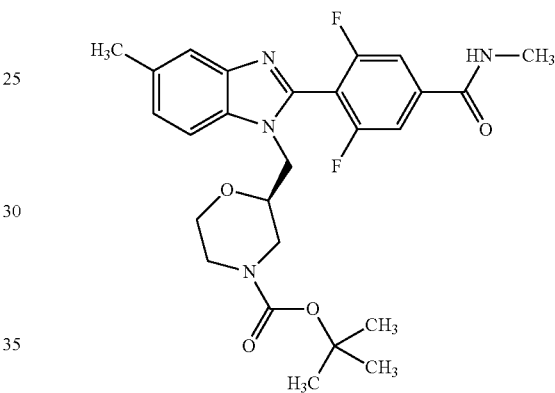

A mixture of (S)-tert-butyl 2-((1,3-dioxoisoindolin-2-yl)methyl)morpholine-4-carboxylate (50 g, 144.35 mmol), ethanolamine (43.7 mL, 721.76 mmol), and 2-methyltetrahydrofuran (250 mL) was stirred at 40° C. under N₂ for 6 hr. Afterward, the temperature was decreased to 25° C. Stirring was then continued for an additional 16 hr. A solution of 5% NaOH in water (250 mL) was added, followed by 2-methyltetrahydrofuran (200 mL). The mixture was stirred for 10 min, and then allowed to settle. The aqueous phase was removed and extracted with 2-methyltetrahydrofuran (250 mL). The organics were combined and washed with a mixture of water (100 mL) and brine (100 mL). The resulting mixture was concentrated under reduced pressure, and then dimethylsulfoxide (110 mL), calcium carbonate (12.51 g, 125.03 mmol), and 4-fluoro-3-nitrotoluene (15.37 mL, 125.03 mmol) were added. After stirring the mixture at 110° C. for 20 hr, it was cooled to 47° C. and sodium dithionite (65.3 g, 375.09 mmol), 3,5-difluoro-4-formyl-N-methylbenzamide (24.9 g, 125.03 mmol), and ethanol (330 mL) were added. The mixture was then stirred at 80° C. for 26 hr, and cooled to 35° C. The mixture was filtered over diatomaceous earth and washed twice with ethanol (50 mL). The filtrate was concentrated under reduced pressure, and the resulting solution was charged back into the reactor. EtOAc (250 mL) and water (150 mL) were added, and the mixture was stirred for 5 min. The phases were then allowed to separate. The aqueous phase was extracted with EtOAc (200 mL), and the combined organic phases were washed with a mixture of water (75 mL) and brine (75 mL). The organic phase was transferred to a round-bottom flask and concentrated under reduced pressure to form a foam, which, in turn, was dried under mechanical vacuum at 45° C. to produce the title compound (58.4 g, 117 mmol, 81%). $^1$H NMR (500 MHz, chloroform-d) δ ppm 1.39 (s, 9H), 2.38 (t, J=11.59 Hz, 1H), 2.50-2.57 (m, 3H), 2.72 (d, J=10.01 Hz, 1H), 3.00 (d, J=4.65 Hz, 3H), 3.23 (br. s., 1H), 3.49-3.82 (m, 4H), 3.82-4.15 (m, 2H), 7.23 (d, J=8.20 Hz, 1H), 7.36-7.49 (m, 3H), 7.63 (s, 1H), 8.96-9.06 (m, 1H).

Part C. Preparation of (S)-methyl 2-((2-(2,6-difluoro-4-(methylcarbamoyl)phenyl)-5-methyl-1H-benzo[d]imidazol-1-yl)methyl)morpholine-4-carboxylate

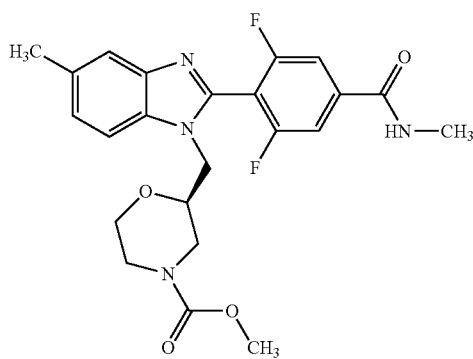

A mixture of (S)-tert-butyl 2-((2-(2,6-difluoro-4-(methylcarbamoyl)phenyl)-5-methyl-1H-benzo[d]imidazol-1-yl)methyl)morpholine-4-carboxylate (58.3 g, 116.5 mmol) and MeOH (65 mL) was stirred at 20° C. as HCl (4.0N aqueous) (300 mL, 1200 mmol) was added. The resulting mixture was stirred for 6 hr, and then dichloromethane (300 mL) was added. The phases were mixed for 5 min and then allowed to settle. The organic phase was removed, and dichloromethane (600 mL) was added. The mixture was stirred at 15° C. as an aqueous solution of 25% NaOH (300 mL) was added over 20 min while maintaining the temperature at less than 25° C. The phases were allowed to settle, and the aqueous phase was removed and extracted with dichloromethane (300 mL). The combined organic phases were concentrated under reduced pressure to a volume of 750 mL. The resulting mixture was cooled to 5° C., and diisopropylethylamine (20.3 mL, 116.38 mmol) was added. Next, methyl chloroformate (9.9 mL, 128.02 mmol) was added over 10 min, keeping the temperature at less than 15° C. After 20 min, the mixture was quenched by adding water (200 mL). The mixture was stirred at 20° C. The phases were then allowed to settle, and the aqueous layer was removed. The organic phase was concentrated under reduced pressure, and MeOH (400 mL) was added. The mixture was stirred at 40° C. while water (500 mL) was added until a turbid mixture was formed. The mixture was heated to 60° C. and then cooled to 43° C., at which point seeds from the title product were added. The temperature was then reduced to 36° C., and the mixture was stirred for 16 hr. The temperature was then reduced to 20° C., and stirring was continued for an additional 16 hr. The solids were recovered by filtration, washed with a 1:9 solution of MeOH/water (50 mL), and dried in the mechanical vacuum at 45° C. for 16 hr to provide (S)-methyl 2-((2-(2,6-difluoro-4-(methylcarbamoyl)phenyl)-5-methyl-1H-benzo[d]imidazol-1-yl)

methyl)morpholine-4-carboxylate (33.9 g, 63%). $^1$H NMR (500 MHz, CHLOROFORM-d) δ ppm 2.47 (br. s., 1H), 2.55 (s, 3H), 2.79 (br. s., 1H), 3.02 (d, J=4.65 Hz, 3H), 3.25 (br. s., 1H), 3.53-3.86 (m, 6H), 3.87-4.15 (m, 3H), 7.24 (d, J=8.12 Hz, 1H), 7.39 (d, J=8.20 Hz, 1H), 7.46 (d, J=8.51 Hz, 2H), 7.65 (s, 1H), 8.73 (br. s., 1 H). The product was analyzed on analytical HPLC MS using a high pH gradient method (mobile phase: 0-95% B; A: H$_2$O with 10 mM NH$_4$OAc in 5% CH$_3$CN, B: CH$_3$CN; 9 min run; X-Bridge C18; column size: 3.00×100 mm; and particle size: 3.5 μm). R$_t$=4.03 min. MS (ESI) m/z calcd for C$_{24}$H$_{24}$F$_2$N$_4$O$_4$ 459.48 [M+H]$^+$. found 459.2.

Example 4

Preparation of (R)-tert-butyl 2-(aminomethyl)morpholine-4-carboxylate

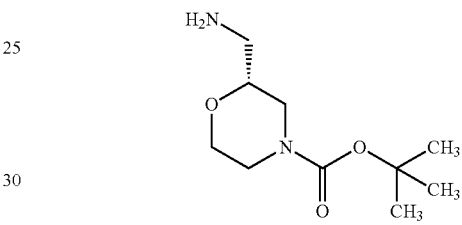

Part A. Preparation of (S)-tert-butyl 2-((methylsulfonyloxy)methyl)morpholine-4-carboxylate

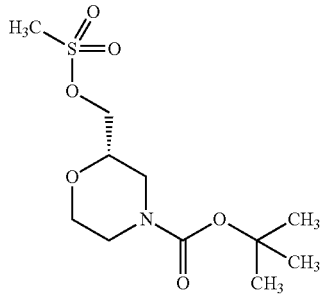 [SMILES: CC(C)(C)OC(=O)N1CCO[C@H](COS(C)(=O)=O)C1]

Methanesulfonyl chloride (12 mL, 0.15 mol) was added to a solution of (S)-tert-butyl 2-(hydroxymethyl)morpholine-4-carboxylate (28 g, 0.13 mmol) in CH$_2$Cl$_2$ (172 mL) and triethylamine (23.4 mL, 0.17 mol) at 0° C. The resulting mixture was stirred at a temperature of from 0° C. to room temperature over 1.5 hr. The mixture was then diluted with water (35 mL), and the phases were separated. The aqueous layer was extracted with CH$_2$Cl$_2$ (3×20 mL). The combined organic layers were washed with brine, dried over MgSO$_4$, and filtered on a pad of silica gel, which was rinsed with CH$_2$Cl$_2$. The filtrate was concentrated under reduced pressure to the title product (37.7 g, 99%) as an oil. $^1$H NMR (300 MHz, CDCl$_3$) δ ppm 1.55 (s, 9H), 2.77-2.91 (m, 1H), 2.97-3.09 (m, 1H), 3.14-3.15 (m, 3H), 3.57-3.67 (m, 1H), 3.73-3.81 (m, 1H), 3.85-4.10 (m, 3H), 4.31 (d, J=4.79 Hz, 2H).

Part B. Preparation of (R)-tert-butyl 2-((1,3-dioxoisoindolin-2-yl)methyl)morpholine-4-carboxylate

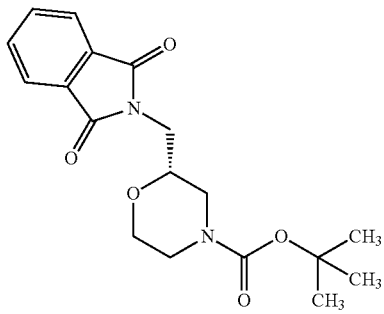 [SMILES: CC(C)(C)OC(=O)N1CCO[C@H](CN2C(=O)c3ccccc3C2=O)C1]

Potassium phthalimide (28.4 g 0.15 mol) was added to a solution of (S)-tert-butyl 2-((methylsulfonyloxy)methyl) morpholine-4-carboxylate (37.7 g, 0.13 mmol) in DMF (256 mL). The resulting mixture was stirred at 110-115° C. for 16 hr, and then cooled to room temperature and poured into water (500 mL). The aqueous layer was extracted with $CH_2Cl_2$ (3×250 mL). The combined organic layers were then washed with brine, dried over $MgSO_4$, filtered, and concentrated under reduced pressure. The residue was diluted in hexanes (200 mL) and then stirred vigorously while adding slowly $Et_2O$ (100 mL). The oil turned into a solid, which was filtered on a Buchner funnel. The filter cake was washed with hexanes and dried under reduced pressure. The mother liquor was concentrated, and the crude residue purified by silica gel flash chromatography (10-60% EtOAc in hexanes) to produce a second crop of solid. Both solids were combined to provide the title compound (38.9 g, 88%). $^1$H NMR (300 MHz, $CDCl_3$) δ ppm 1.45 (s, 9 H), 2.68-2.82 (m, 1H), 2.91-3.04 (m, 1H), 3.44 (dt, J=11.45, 2.81 Hz, 1H), 3.63-3.79 (m, 3H), 3.82-4.03 (m, 3H), 7.70-7.78 (m, 2H), 7.84-7.88 (m, 2H).

Part C. Preparation of (R)-tert-butyl 2-(aminomethyl)morpholine-4-carboxylate

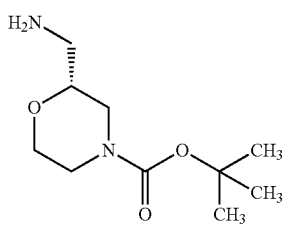

A solution of (R)-tert-butyl 2-((1,3-dioxoisoindolin-2-yl)methyl)morpholine-4-carboxylate (37.9 g, 0.11 mol) in ethanolamine (250 mL) was stirred at room temperature for 16 hr. Afterward, the mixture was poured into water (500 mL). The aqueous layer was extracted with EtOAc (3×250 mL), and then the combined organic layers were washed with brine, dried over $MgSO_4$, filtered, and concentrated under reduced pressure. The residue was purified by silica gel flash chromatography (100% EtOAc then 0-10% MeOH in $CH_2Cl_2$ (with 1% $NH_4OH$)) to provide the title compound (17.2 g, 73%) as an oil. HRMS (ESI) m/z calcd for $C_{10}H_{20}N_2O_3$ 217.15 $[M+H]^+$. found 217.28. $^1$H NMR (300 MHz, $CDCl_3$) δ ppm 1.28 (s, 2H), 1.46 (s, 9H), 2.56-2.70 (m, 1H), 2.73-2.76 (m, 2H), 2.85-2.98 (m, 1 H), 3.30-3.39 (m, 1H), 3.52 (td, J=11.61, 2.82 Hz, 1H), 3.78-3.95 (m, 3H).

Example 5

Preparation of (R)-methyl 2-((2-(2,6-difluoro-4-(methylcarbamoyl)phenyl)-5-methyl-1H-benzo[d]imidazol-1-yl)methyl)morpholine-4-carboxylate

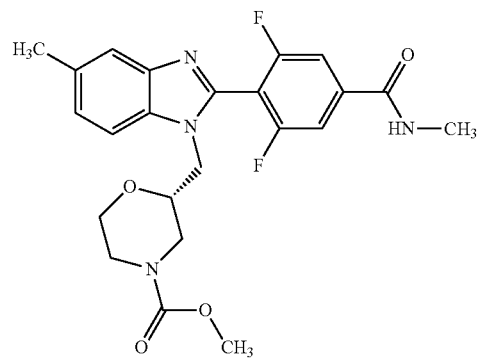

Part A. Preparation of (R)-tert-butyl 2-((2-amino-4-methylphenylamino)methyl)morpholine-4-carboxylate

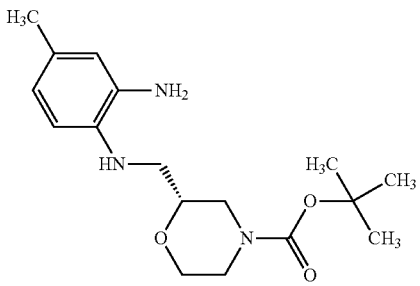 [SMILES: Cc1ccc(NC[C@@H]2CN(C(=O)OC(C)(C)C)CCO2)c(N)c1]

A mixture of (R)-tert-butyl 2-(aminomethyl)morpholine-4-carboxylate (0.715 g, 3.31 mmol), DIPEA (0.577 mL, 3.31 mmol), and 1-fluoro-4-methyl-2-nitrobenzene (0.513 g, 3.31 mmol) in MeOH (14 mL) was heated at 140° C. in A microwave reactor for 30 min and then cooled to room temperature. Acetic acid (1.9 mL, 33.1 mmol) was added, followed by zinc (2.162 g, 33.1 mmol). The resulting mixture was stirred at room temperature for 90 min to afford the (R)-tert-butyl 2-((2-amino-4-methylphenylamino)methyl)morpholine-4-carboxylate product (1.06 g), which was used without further purification in the next step. The product was analyzed on analytical HPLC MS using the high pH gradient method (mobile phase: 5-95% B; A: $H_2O$ with 10 mM $NH_4CO_3$ and 0.375% $NH_4OH$ v/v; B: $CH_3CN$; 2.25 min run; X-Bridge C18; column size: 2.1×30 mm; and particle size: 5 µm). MS m/z 322.4 [M+H]+ (ESI), R_t 1.80 min.

Part B. Preparation of (R)-4-(1-((4-(tert-butoxycarbonyl)morpholin-2-yl)methyl)-5-methyl-1H-benzo[d]imidazol-2-yl)-3,5-difluorobenzoic acid

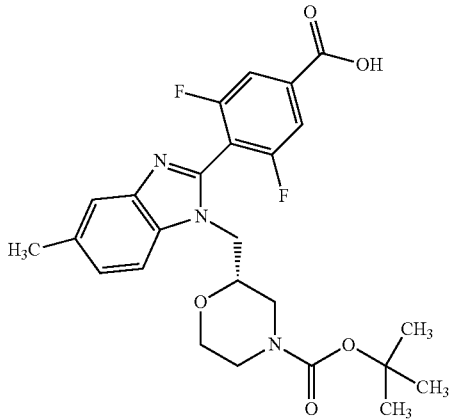 [SMILES: Cc1ccc2c(c1)nc(-c1c(F)cc(C(=O)O)cc1F)n2C[C@@H]1CN(C(=O)OC(C)(C)C)CCO1]

A mixture of (R)-tert-butyl 2-((2-amino-4-methylphenylamino)methyl)morpholine-4-carboxylate (600 mg, 1.87 mmol), 3,5-difluoro-4-formylbenzoic acid (347 mg, 1.87 mmol) and acetic acid (0.534 ml, 9.33 mmol) in methanol (15.0 ml) was stirred for 1.5 hr at room temperature. The mixture was then concentrated under reduced pressure, and the residue was purified by silica gel flash chromatography, eluting with mixtures of EtOAc and heptane, to afford (R)-4-(1-((4-(tert-butoxycarbonyl)morpholin-2-yl)methyl)-5-methyl-1H-benzo[d]imidazol-2-yl)-3,5-difluorobenzoic acid (750 mg, 82%) as an oil. The oil was analyzed on analytical HPLC MS using the high pH gradient method (mobile phase: 5-95% B; A: H₂O with 10 mM NH₄CO₃ and 0.375% NH₄OH v/v; B: CH₃CN; 2.25 min run; X-Bridge C18; column size: 2.1×30 mm; particle size: 5 µm). MS m/z 488.4 [M+H]+ (ESI), R_t 1.56 min.

Part C. Preparation of (R)-tert-butyl 2-((2-(2,6-difluoro-4-(methylcarbamoyl)phenyl)-5-methyl-1H-benzo[d]imidazol-1-yl)methyl)morpholine-4-carboxylate

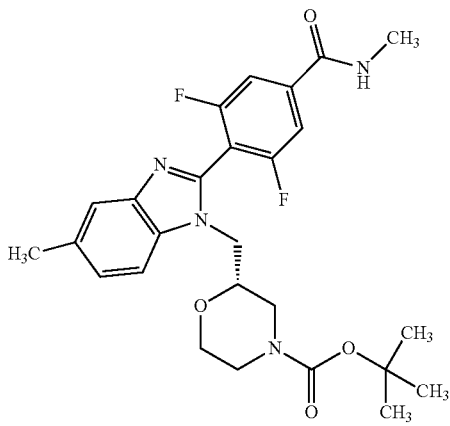 [SMILES: CNC(=O)c1cc(F)c(-c2nc3cc(C)ccc3n2C[C@@H]2CN(C(=O)OC(C)(C)C)CCO2)c(F)c1]

(R)-4-(1-((4-(tert-butoxycarbonyl)morpholin-2-yl)methyl)-5-methyl-1H-benzo[d]imidazol-2-yl)-3,5-difluorobenzoic acid (750 mg, 1.54 mmol) was added to DMT-MM (408 mg, 1.69 mmol) in DMF (30.00 mL) under N₂. The resulting suspension was stirred for 30 min. Afterward, methylamine 33% (by weight) solution in absolute ethanol (0.458 mL, 1.69 mmol) was added, and the mixture was stirred for 3 hr. The mixture was then concentrated under reduced pressure, and the resulting residue was dissolved in EtOAc and washed sequentially with water and brine. The organic layer was dried over MgSO₄, filtered, and concentrated under reduced pressure. The crude material was purified on preparative HPLC MS using the short high pH shallow gradient method (mobile phase: 30-50% B; A: H₂O with 10 mM NH₄CO₃ and 0.375% NH₄OH v/v; B: CH₃CN; 10 min run; XBridge Prep C18 OBD, Waters reverse phase column; column size: 30×50 mm; and particle size 5 µm). This produced (S)-tert-butyl 2-((2-(2,6-difluoro-4-(methylcarbamoyl)phenyl)-5-methyl-1H-benzo[d]imidazol-1-yl)methyl)morpholine-4-carboxylate as an oil, which was used without further purification (1.4 g, >100% yield) in the next step. The oil was analyzed on analytical HPLC MS using the high pH gradient method (mobile phase: 5-95% B; A: H₂O with 10 mM NH₄CO₃ and 0.375% NH₄OH v/v; B: CH₃CN; 2.25 min run; X-Bridge C18; column size: 2.1×30 mm, particle size: 5 µm). MS m/z 501.4 [M+H]+ (ESI), R_t 1.85 min.

Part D. Preparation of (S)-3,5-difluoro-N-methyl-4-(5-methyl-1-(morpholin-2-ylmethyl)-1H-benzo[d]imidazol-2-yl)benzamide trifluoroacetic acid salt

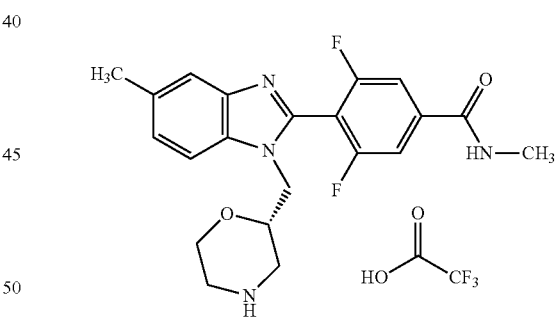

(R)-tert-butyl 2-((2-(2,6-difluoro-4-(methylcarbamoyl)phenyl)-5-methyl-1H-benzo[d]imidazol-1-yl)methyl)morpholine-4-carboxylate (770 mg, 1.54 mmol) was dissolved in DCM (10.0 mL). Afterward, TFA (2.00 mL) was added to the mixture at 0° C. The resulting mixture was stirred at room temperature for 1 hr and then concentrated under reduced pressure. The crude (S)-3,5-difluoro-N-methyl-4-(5-methyl-1-(morpholin-2-ylmethyl)-1H-benzo[d]imidazol-2-yl)benzamide trifluoroacetic acid salt product was used without further purification (790 mg) in the next step. It was analyzed on analytical HPLC MS using the high pH gradient method (mobile phase: 5-95% B; A: H₂O with 10 mM NH₄CO₃ and 0.375% NH₄OH v/v; B: CH₃CN; 2.25 min run; X-Bridge C18; column size: 2.1×30 mm; particle size: 5 μm). MS m/z 401.3 [M+H]+ (ESI), $R_t$ 1.37 min.

Part E. Preparation of (R)-methyl 2-((2-(2,6-difluoro-4-(methylcarbamoyl)phenyl)-5-methyl-1H-benzo[d]imidazol-1-yl)methyl)morpholine-4-carboxylate

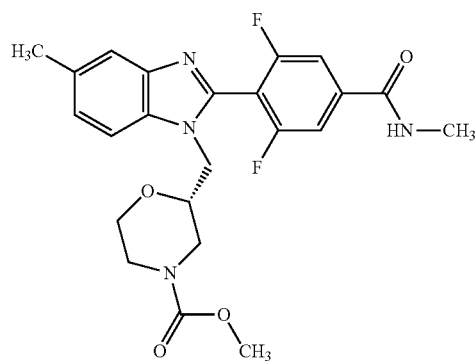

A mixture of (S)-3,5-difluoro-N-methyl-4-(5-methyl-1-(morpholin-2-ylmethyl)-1H-benzo[d]imidazol-2-yl)benzamide trifluoroacetic acid salt (150 mg, 0.37 mmol), methyl chloroformate (0.058 mL, 0.75 mmol), and N,N-diisopropylethylamine (0.072 mL, 0.41 mmol) in DCM (10.00 mL) was stirred at room temperature for 30 min. The mixture was then concentrated under reduced pressure, and the residue was purified on preparative HPLC MS using the short high pH shallow gradient method (mobile phase: 30-50% B; A: $H_2O$ with 10 mM $NH_4CO_3$ and 0.375% $NH_4OH$ v/v; B: $CH_3CN$; 10 min run; XBridge Prep C18 OBD, Waters reverse phase column; column size: 30×50 mm; particle size: 5 μm). This produced to afford (R)-methyl 2-((2-(2,6-difluoro-4-(methylcarbamoyl)phenyl)-5-methyl-1H-benzo[d]imidazol-1-yl)methyl)morpholine-4-carboxylate (41.7 mg, 24% yield) as a solid. The solid was analyzed on analytical HPLC MS using the high pH gradient method (mobile phase: 5-95% B; A: $H_2O$ with 10 mM $NH_4CO_3$ and 0.375% $NH_4OH$ v/v; B: $CH_3CN$; 2.25 min run; X-Bridge C18; column size: 2.1×30 mm; and particle size: 5 μm). MS m/z 459.3 [M+H]+ (ESI), $R_t$ 1.58 min. $^1H$ NMR (400 MHz, methanol-d4) δ ppm 2.50 (s, 3H) 2.54 (dd, J=4.49, 3.71 Hz, 1H) 2.69-2.84 (m, 1H) 2.96 (s, 3H) 3.25 (td, J=11.91, 2.73 Hz, 1H), 3.55-3.64 (m, 2H), 3.66 (s, 3H), 3.74 (d, J=12.89 Hz, 1H), 3.96 (d, J=12.89 Hz, 1H), 4.16 (dd, J=15.23, 7.42 Hz, 1H), 4.37 (dd, J=15.23, 3.12 Hz, 1H), 7.26 (dd, J=8.59, 1.17 Hz, 1H), 7.53 (s, 1H), 7.58 (d, J=8.59 Hz, 1H), 7.64 (d, J=8.59 Hz, 2H). HRMS m/z calcd for $C_{23}H_{25}F_2N_4O_4$ 459.1838 [M+H]+. found 459.1849.

Example 6

Biological Evaluation of Compounds as Antagonists at Human P2X3 Receptor In Vitro The antagonist properties of compounds in the present invention were assayed as inhibitors of intracellular calcium increase induced by activation of hP2X3 (human Purinergic P2X receptors subtype 3, accession number AB016608 for clone A and accession number NM_002559 for clone B), expressed in RLE cells (rat liver endothelium, ATCC. The RLE/hP2X3 cells were grown in William's medium 1× (Gibco, 12551-032), supplemented with 10% Fetal bovine serum (Wisent, 090850), 2 mM L-Glutamine (Wisent, 609-065-EL), and 600 μg/mL Geneticin G-418 (Wisent, 61234) in a humidified incubator (5% $CO_2$ and 37° C.).

Method 1

In one assay, Fluo-4 assay on FDSS7000 (Hamamatsu) was performed using cryopreserved RLE cells stably expressing hP2X3 plated in 384 well plates, 24 hr before the experiment at a density appropriate for obtaining the desired final confluence. After processing the cell plates with Fluo-4 and performing a subsequent incubation followed by washing steps, a double addition was carried out. The first addition included the test compounds diluted in HBSS buffer containing 2 mM $CaCl_2$ preincubated for 20 min before a second addition. The second addition included 2 uM of ATP. Calcium mobilization was measured with the FDSS7000 over a time lapse of 3 min, and fluorescent counts were exported for analysis. This resulted in a $pIC_{50}$, which was calculated in Activity base with ExcelFit. Hill coefficients and % inhibitions can also be determined.

Method 2

In another assay, a procedure similar to Method 1 was used on RLE cells stably expressing hP2X3. In this method, however, α,β methylene-ATP (Sigma M6517) was used instead of ATP as the hP2X3 agonist.

Method 3

In a third assay, hP2X3-expressing cells were maintained in culture and the day before the experiment, the cells were plated in 384-black polylysine coated plates (Becton/Dickinson, 356663) at 8000 cells/well in 50 μL/well in William's medium without Geneticin, and then placed in an incubator for 24 hr. On the day of the experiment, the cells and test compounds were prepared as follows. For the compounds, α,β-methylene-ATP (500 nM, final concentration) and reference compounds (spanning a range of 10 dilutions, three-fold apart) were diluted, at a concentration 4-fold higher than the desired final concentration, into the hP2X3 assay buffer (125 mM Choline chloride, 5 mM Glucose, 0.2 g/L BSA, 25 mM Hepes, 5 mM KCl, 1 mM $MgCl_2$, 1.5 mM $CaCl_2$, pH 7.4) or alternatively in the rat P2X3 & rat P2X2/3 assay buffer (HBSS: 125 mM NaCl, 5 mM Glucose, 0.2 g/L BSA, 25 mM Hepes, 5 mM KCl, 1 mM $MgCl_2$, 1.5 mM $CaCl_2$, pH 7.4). After preparing the compounds, the medium was removed from the cell plates by inversion. A loading solution of 30 μL assay buffer containing 4 μM of the calcium indicator dye FLUO-4 AM (Molecular Probes F14202) was added to each well using a Multidrop (Labsystems). The cell plates were then incubated at room temperature for 30-40 min to allow loading of the dye into the cells. The incubation was terminated by washing the cells four times in assay buffer using a Skatron Embla (Molecular Devices), and leaving 25 μL of assay buffer in each well. Cell plates were then transferred to the FLIPR. Experiments were initiated by measuring a baseline fluorescence reading for 10 sec, followed by adding 12.5 μL of compounds and data sampling for a total 280 seconds. The experiments were terminated by adding 12.5 μL of a reference agonist (500 nM α,β-methylene-ATP) or buffer, producing a final assay volume of 50 μL, and data sampling for an additional 280 seconds. During entire experiment, fluorescence emission was read by the FLIPR on board CCD camera using filter with emission wavelength of 520-545 nm. This resulted in a pIC50, which was calculated in Activity base with ExcelFit. Hill coefficients and % inhibitions can also be determined.

IC$_{50}$'s obtained using the above methods are shown in Table 1.

TABLE 1

IC$_{50}$'s Observed for the Compounds of Examples 3 and 5

| Ex | Human P2X3 IC$_{50}$ (μM) Method 1 | Human P2X3 IC$_{50}$ (μM) Method 2 | Human P2X3 IC$_{50}$ (μM) Method 3 |
|---|---|---|---|
| 3 | 0.007 | 0.014 | 0.016 |
| 5 | | | 0.016 |

Unless otherwise indicated, the following definitions are to be used when reading this patent:

The chemical nomenclature used in this patent generally follows the examples and rules stated in *Nomenclature of Organic Chemistry, Sections A, B, C, D, E, F, and H*, Pergamon Press, Oxford, 1979.

The term "pharmaceutically acceptable" is used to characterize a moiety (e.g., a salt, dosage form, carrier, diluent, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

"d" means doublet.
"DCM" means dichloromethane.
"dd" means doublet of doublet.
"DMEA" means dimethylethylamine.
"DMF" means N,N-dimethyl formamide.
"DMSO-d$_6$" means dimethylsulfoxide-d$_6$.
"DMT-MM" means 4-(4,6-Dimethoxy-1,3,5-triazin-2-yl)-4-methylmorpholinium chloride.
"ESI" means electrospray ionization.
"Et" means ethyl.
"EtOAc" means ethyl acetate.
"EtOH" means ethanol.
"Ex" means example.
"g" means gram.
"hr" means hour or hours.
"$^1$H NMR" means proton nuclear magnetic resonance.
"HPLC" means high-performance liquid chromatography.
"HRMS" means high-resolution mass spectrometry.
"L" means liter.
"LCMS" means liquid chromatography/mass spectroscopy.
"m" means multiplet.
"M" means molar.
"mL" means milliliter.
"Me" means methyl.
"MeCN" means acetonitrile.
"MeOH" means methanol.
"mg" means milligram.
"MHz" means megahertz.
"min" means minute or minutes.
"mmol" means millimole.
"mol" means mole.
"MS" means mass spectrometry.
"MTBE" means methyl tert-butyl ether.
"N" means normal.
"ppm" means parts per million.
"Pr" means propyl.
"q" means quartet.
"qt" means quintet.
"R$_t$" means retention time (HPLC).
"s" means singlet.
"SFC" means supercritical-fluid chromatography.
"t" means triplet.
"TFA" means trifluoroacetic acid.
"TLC" means thin layer chromatography.
"TMEDA" means N,N,N',N'-tetramethyl-1,2-ethylenediamine.
"UV" means ultraviolet.
"vol" means volume.

References made in the singular may also include the plural. For example, "a" and "an" may refer to either one or more than one.

The words "comprise," "comprises," and "comprising" in this patent (including the claims) are to be interpreted inclusively rather than exclusively. This interpretation is intended to be the same as the interpretation that these words are given under United States patent law.

The above description of illustrative embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A compound of Formula I or a salt thereof, wherein the compound of Formula I corresponds to:

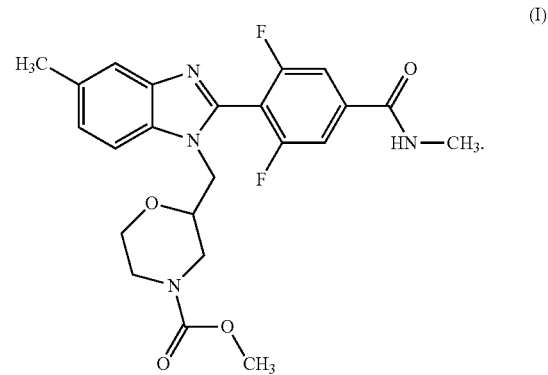 [SMILES: CNC(=O)c1cc(F)c(-c2nc3cc(C)ccc3n2CC2CN(C(=O)OC)CCO2)c(F)c1]

(I)

2. A compound or salt thereof according to claim 1, wherein the compound corresponds to Formula II:

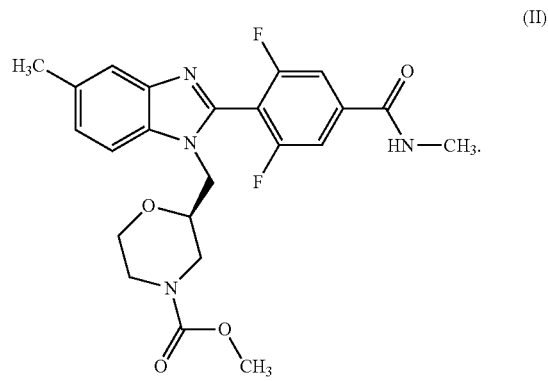 [SMILES: CNC(=O)c1cc(F)c(-c2nc3cc(C)ccc3n2C[C@H]2CN(C(=O)OC)CCO2)c(F)c1]

(II)

3. A compound or salt thereof according to claim 1, wherein the compound corresponds to Formula III:

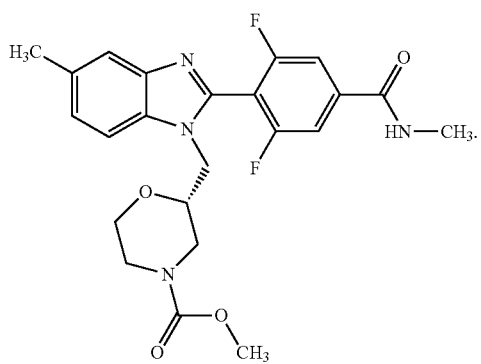

(III)

4. A pharmaceutical composition, wherein the composition comprises:
   a compound according to claim 1 or a pharmaceutically acceptable salt thereof; and
   a carrier, diluent, or excipient.

5. A kit, wherein the kit comprises:
   a compound or salt according to claim 1; and
   an apparatus for administering the compound or salt to an animal patient;
   instructions for administering the compound or salt to an animal patient; a carrier, diluent, or excipient; or a pharmaceutically active ingredient other than the compound or salt.

6. A method of inhibiting P2X3 activity for the treatment of a disorder associated with P2X3 activity in an animal in need of such treatment, wherein the method comprises administering to the animal a therapeutically effective amount of a compound according to claim 1 or a pharmaceutically acceptable salt thereof.

7. A method for treating pain in an animal in need of such treatment, wherein the method comprises administering to the animal a therapeutically effective amount of a compound according to claim 1 or a pharmaceutically acceptable salt thereof.

8. A method for treating a urinary tract disorder in an animal in need of such treatment, wherein the method comprises administering to the animal a therapeutically effective amount of a compound according to claim 1 or a pharmaceutically acceptable salt thereof.

9. A method according to claim 8, wherein the urinary tract disorder comprises an overactive bladder.

10. A method according to claim 6, wherein the animal is a human.

11. A method according to claim 7, wherein the animal is a human.

12. A pharmaceutical composition, wherein the composition comprises:
    a compound according to claim 2 or a pharmaceutically acceptable salt thereof; and
    a carrier, diluent, or excipient.

13. A pharmaceutical composition, wherein the composition comprises:
    a compound according to claim 3 or a pharmaceutically acceptable salt thereof; and
    a carrier, diluent, or excipient.

14. A method of inhibiting P2X3 activity for the treatment of a disorder associated with P2X3 activity in an animal in need of such treatment, wherein the method comprises administering to the animal a therapeutically effective amount of a compound according to claim 2 or a pharmaceutically acceptable salt thereof.

15. A method according to claim 14, wherein the animal is a human.

16. A method for treating pain in an animal in need of such treatment, wherein the method comprises administering to the animal a therapeutically effective amount of a compound according to claim 2 or a pharmaceutically acceptable salt thereof.

17. A method according to claim 16, wherein the animal is a human.

18. A method for treating a urinary tract disorder in an animal in need of such treatment, wherein the method comprises administering to the animal a therapeutically effective amount of a compound according to claim 2 or a pharmaceutically acceptable salt thereof.

19. A method according to claim 18, wherein the animal is a human.

20. A method according to claim 18, wherein the urinary tract disorder comprises an overactive bladder.

21. A method according to claim 20, wherein the animal is a human.

22. A method of inhibiting P2X3 activity in the treatment of a disorder associated with P2X3 activity in an animal in need of such treatment, wherein the method comprises administering to the animal a therapeutically effective amount of a compound according to claim 3 or a pharmaceutically acceptable salt thereof.

23. A method according to claim 22, wherein the animal is a human.

24. A method for treating pain in an animal in need of such treatment, wherein the method comprises administering to the animal a therapeutically effective amount of a compound according to claim 3 or a pharmaceutically acceptable salt thereof.

25. A method according to claim 24, wherein the animal is a human.

26. A method for treating a urinary tract disorder in an animal in need of such treatment, wherein the method comprises administering to the animal a therapeutically effective amount of a compound according to claim 3 or a pharmaceutically acceptable salt thereof.

27. A method according to claim 26, wherein the animal is a human.

28. A method according to claim 27, wherein the urinary tract disorder comprises an overactive bladder.

29. A method according to claim 28, wherein the animal is a human.

* * * * *